United States Patent
Feistel

[19]

[11] Patent Number: 6,136,549
[45] Date of Patent: Oct. 24, 2000

[54] SYSTEMS AND METHODS FOR PERFORMING MAGNETIC CHROMATOGRAPHY ASSAYS

[76] Inventor: Christopher C. Feistel, 255 Cypress Dr. No. 1, Laguna Beach, Calif. 92651

[21] Appl. No.: 09/418,864

[22] Filed: Oct. 15, 1999

[51] Int. Cl.[7] .......................... G01N 33/53; G01N 33/553
[52] U.S. Cl. ..................... 435/7.1; 435/2; 435/5; 435/7.21; 435/7.32; 435/239; 435/803; 435/287.2; 435/207.7; 435/287.9; 435/805; 435/810; 435/970; 436/513; 436/512; 436/518; 436/531; 436/526; 436/533; 436/538; 436/806; 436/824; 422/56
[58] Field of Search ........................... 435/2, 5, 7.1, 7.21, 435/7.32, 239, 803, 287.2, 287.7, 287.9, 805, 810, 970; 436/513, 512, 518, 531, 526, 533, 538, 806, 824; 422/56

[56] References Cited

U.S. PATENT DOCUMENTS

| | | | |
|---|---|---|---|
| 4,410,660 | 10/1983 | Straus ........................................ 525/54.1 |
| 4,578,716 | 3/1986 | Vanrijckevorsel et al. .................. 360/1 |
| 4,710,472 | 12/1987 | Saur et al. ............................... 435/287 |
| 4,731,337 | 3/1988 | Luotola et al. . |
| 4,777,145 | 10/1988 | Luotola et al. . |
| 4,935,147 | 6/1990 | Ullman et al. . |
| 5,035,862 | 7/1991 | Dietze et al. ........................... 422/68.1 |
| 5,075,078 | 12/1991 | Osikowicz et al. . |
| 5,238,811 | 8/1993 | Fujiwara et al. . |
| 5,252,459 | 10/1993 | Tarcha et al. ............................... 435/6 |
| 5,384,264 | 1/1995 | Chen et al. . |
| 5,508,164 | 4/1996 | Kausch et al. ............................. 435/6 |
| 5,612,222 | 3/1997 | Gordon et al. ............................ 436/5 |
| 5,643,722 | 7/1997 | Rothschild et al. ....................... 435/6 |
| 5,658,723 | 8/1997 | Oberhardt ................................. 435/4 |
| 5,712,170 | 1/1998 | Kouvonen et al. ..................... 436/518 |
| 5,750,333 | 5/1998 | Clark ......................................... 435/5 |
| 5,770,388 | 6/1998 | Vorpahl . |
| 5,795,784 | 8/1998 | Arnquist et al. ......................... 436/50 |
| 5,800,994 | 9/1998 | Martinell et al. ......................... 435/6 |
| 5,817,458 | 10/1998 | King et al. . |
| 5,821,073 | 10/1998 | Lee . |
| 5,856,092 | 1/1999 | Dale et al. ................................ 435/6 |
| 5,874,216 | 2/1999 | Mapes . |
| 5,876,935 | 3/1999 | Pankratz et al. .......................... 435/6 |
| 5,879,549 | 3/1999 | Caiozza ................................. 210/186 |
| 5,882,863 | 3/1999 | Imai et al. ................................ 435/6 |
| 5,888,748 | 3/1999 | Crabb et al. ........................... 435/7.3 |
| 5,922,537 | 7/1999 | Ewart et al. .............................. 435/6 |
| 5,925,573 | 7/1999 | Colin et al. ............................. 436/525 |
| 5,965,375 | 10/1999 | Vlkirs . |

OTHER PUBLICATIONS

Molday et al. 1984. Separation of cells labeled with immunospecific iron dextran mocrospheres using gradient magnetic chromatography. FEBS Letters. 170:232–238.

Molday et al. 1982. Immunospecific ferromagnetic iron–dextran reagents for the labeling and magnetic separation of cells. J. Immunol. Methods. 52:353–367.

Carlberg, David L.; Lateral–Flowassays:DesigningFor Automation May/Jun. 1999; PGS 48–55; IVD Technology.

*Primary Examiner*—Christopher L. Chin
*Assistant Examiner*—Minh-Quan K. Pham
*Attorney, Agent, or Firm*—Stetina Brunda Garred & Brucker

[57] ABSTRACT

Novel magnetic assay methods and systems, as well as systems for conducting spectrophotometric analysis therewith. According to a preferred embodiment, the magnetic assay methods and systems incorporate a chromatographic medium, such as an assay test strip, that is designed to be contacted with a test solution having activated magnetic particles. A magnetic field, generated by a magnet or electromagnet, is additionally provided that if selectively applied to a chromatographic medium which causes the charged particles to become substantially bound at a site all in the chromatographic medium specified by the position of the magnets, to thus form a captured line or zone. To the degree of magnetic force applied to the medium may be selectively adjusted to vary the width or surface area of the capture line or zone. Additionally, in a preferred embodiment, capture lines may be formed while test strips are in motion along a stationary magnetized rail. Spectrophotometric analysis may be made at the captured lines and zones for qualitative and quantitative analysis of unidentifiable analyte. A multimode photometer consisting of an optical canopy and base that defines an optical chamber may be utilized for conducting spectral or multi-spectral analysis.

19 Claims, 5 Drawing Sheets

SYSTEMS AND METHODS FOR PERFORMING MAGNETIC CHROMATOGRAPHY ASSAYS

CROSS-REFERENCE TO RELATED APPLICATIONS (Not Applicable)

STATEMENT RE: FEDERALLY SPONSORED RESEARCH/DEVELOPMENT (Not Applicable)

BACKGROUND OF THE INVENTION

Ligand-receptor assays or immunoassays are well-known in the art. Since their introduction in 1971, such assays have been utilized in a variety of applications to detect minute amounts of hormones, drugs, antibodies, and other substances suspected of being present in a given fluid sample. In this regard, researchers equipped with enzymes, antibodies, gene probes, and other reagents have made it possible to create chemical detection schemes for almost any compound of interest in a great diversity of applications. Among these applications are: commercial production of pharmaceuticals and food stuffs; food safety; diagnosis and treatment of disease in medical, veterinary, and agricultural environs; and detection and eradication of toxins in the environment. Common to all such applications is the requirement that chemical detection be performed in a timely, reliable, and cost effective manner.

Generally, bioassay schemes are developed and commercialized in formats suitable for use in laboratories equipped with general purpose instrumentation. Examples of these formats include immunoassay and DNA hybridization performed in test tubes, cuvettes, microtiter plates, columns, and electrophoretic gels. These formats usually include elaborate operational procedures and require frequent calibration using several calibrants which contain the analyte of interest at different concentrations. As a consequence, the high cost and complexity of operation associated with such formats limits widespread utilization thereof.

To address such drawbacks, developers and end users of immunoassays are increasingly replacing conventional bioassay formats which use test tubes, cuvettes, microtiter plates, columns, and electrophoretic gels with thin film chromatographic devices known as test strips. As is known in the art, the majority of test strips used for immunochemical detection of compounds are so called lateral flow test strips in which sample and reagents flow within the plane of the test strip. Advantageously, assays configured in a test strip format can produce rapid results, are simpler to operate, and are more cost-effective than conventional formats. Additionally, such test strip assays may be utilized by unskilled laborers and can produce results on-site (i.e., outside a laboratory facility).

Generally, such assays rely on the binding of analytes by receptors to determine the concentration of such analytes in a given sample and are typically characterized as either competitive or non-competitive. Non-competitive assays generally utilize receptors in substantial excess over the concentration of analytes to be determined in the assay. Typical of such non-competitive immunoassays include sandwich assays, which detect the presence of an analyte by binding two receptors thereto. In such arrangement, the first receptor, which is typically an antibody is bound to a solid phase such that when the analyte is present, such analyte becomes affixed thereto. A second receptor having a label covalently attached thereto, which may comprise a radioactive, fluorescent, enzymatic, dye or other detectable moiety (collectively referred to as tracers), is introduced to the assay which consequently binds to the bound ligand, to the extent the ligand is present, and thereafter produces a signal consistent with the presence of such ligand. If the sample does not contain the molecules of interest, the labeled receptor is carried past the immobilized receptor without reacting which, as a consequence, will not cause a change in the membrane. Such non-competitive immunoassays are primarily useful for the detection of large molecules such as proteins, large hormones or molecules which have multiple binding sites, such as human chorionic gonadotropin (HCG) and typically will not work with small molecules that have only one binding site.

Competitive assays, in contrast, generally involve competition between a ligand present in a given sample, and a ligand analog having a tracer/label covalently linked thereto to permit detection for a limited number of binding sites provided by the ligand receptor, which typically comprises an antibody bound to a solid phase. Such assays are particularly suited to detect smaller molecules, such as drugs and drug metabolites. In this context, drug analogs are utilized that have been covalently bound to a protein which is then immobilized on a membrane. Antibody specific to the drug is then labeled and immobilized on a porous pad. When a sample is added which is suspected of containing a given analyte, such sample dissolves the labeled antibody and carries it into contact with the immobilized drug-protein region. If there is little or no drug in the sample, a large amount of the labeled antibody is bound to the immobilized drug-protein region which, consequently, produces a detectable signal. If the sample contains a high amount of drug, little or no labeled antibody is bound to the immobilized drug-protein region and thus in turn gives little or no signal.

Today, rapid immunoassays generally consists of an adhesive-covered plastic backing onto which several porous pads and a piece of protein-binding membrane are attached. The membrane typically contains a section that has been impregnated with a binding partner (i.e., a receptor or ligand analog). A second pad is typically provided which contains a labeled target molecule or labeled antibody protein-binding membrane. When a sample suspected of containing a target ligand is contacted with the immunoassay, such sample dissolves the labeled element or tracer and the capillary action of the protein-binding membrane subsequently draws the sample with tracer dissolved therein into contact with the impregnated binding partner. When this reaction occurs, there is a change in the appearance of the binding membrane, with the difference providing a qualitative indication of the presence or absence of the ligand suspected of being present in such sample.

Typical examples of this form of test strip are those which visually display two parallel lines (known as capture lines) on a test membrane. Capture lines consist of immobilized capture reagents or receptors which are preapplied to the test membrane during its manufacture. In this regard, both virtually all prior art assays, whether competitive or non-competitive, typically deploy a receptor immobilized on a membrane, as assessed above. A schematic representation of the construction of a typical lateral flow test strip is as follows:

reagent pad//test membrane/capture line/test membrane/capture line/test membrane//absorbent pad where:
symbol / designates a phase boundary within a single chromatographic medium; and
symbol // designates a union of two separate mediums (chromatographic or other medium).

One of the two capture lines serves as an indication that the test strip performance has not been compromised. In this regard, such capture line serves an important function by providing quality assurance and integrity of the assay, which is generally considered necessary insofar as individual test strip performance can vary greatly. The second of such capture lines becomes visible only when the sample contains an amount of analyte in excess of a minimum concentration (threshold concentration). Exemplary of such prior art systems and methodologies include the immunoassay systems and test strips disclosed in U.S. Pat. No. 5,658,723, issued on Aug. 19, 1997, to Oberhardt entitled "Immunoassay System Using Forced Convection Currents" and U.S. Pat. No. 5,712,170, issued on Jan. 27, 1998, to Kouvonen, et al. entitled "Test Strip, Its Production and Use", the teachings of each of which are expressly incorporated herein by reference.

Unfortunately, despite their cost-effectiveness and simplicity of use, typical test strip format assays are less accurate, less precise, and less sensitive to analyte presence than conventional formats. As a result of such drawbacks, the application of test strip format assays has been limited to semi-quantitative or qualitative assays. Among the more significant factors that contribute to the inaccuracy and imprecision of test strip format assays include the manufacture and use of capture lines. As is widely recognized, the manufacture of consistently uniform capture lines requires elaborate material control and manufacturing processes with rigid specifications that must operate within narrow tolerances. Moreover, to function properly, most test strip formats require that the analytes to be detected must be uniformly captured in a precise geometry at a precise location on the test strip and that factors such as the ambient humidity present at the time of test strip manufacture, type of membrane utilized in such manufacturing process, and a capture reagent-receptor itself contributing greatly to assay inaccuracies and false readings. A detailed discussion regarding the drawbacks associated with the binding of protein capture reagents in immunochromatographic assays can be found in Jones, Kevin D., *"Troubleshooting Protein Binding in Nitrocellulose Membranes"*, Part I, IVD Technology, Volume V, No. II, March–April 1999, pages 32–41 and Part II, IVD Technology, Volume V, No. III, May–June 1999, pages 26–35, the teachings of which are expressly incorporated herein by reference.

It is therefore desirable to devise an alternative lateral flow device which can capture analyte at a precise location and in a precise geometry without the use of preapplied capture lines. There is further a need for an assay that has greater sensitivity in reproduceability than prior art assays and methods and is likewise inexpensive, relatively easy to manufacture, and capable of being utilized for a wide variety of applications. There is still further a need in the art for such an assay that can identify the presence of two or more suspect ligands in a given sample. It is also desirable to devise an analytical instrument which can provide a quantitative analysis of a captured analyte on a lateral flow assay device.

BRIEF SUMMARY OF THE INVENTION

The present invention specifically addresses and alleviates to the above-identified deficiencies in the art. In this regard, the present invention pertains to several novel bioassay methodologies, chromatographic devices, and an optional multimode photometer/analyzer which together can perform bioassays with accuracy and precision like that of conventional laboratory formats while retaining the operational simplicity, rapid analysis, and cost-effectiveness like that of test strip formats. The chromatographic devices and novel bioassay methodologies of the present invention further minimize problems associated with the manufacture of test strips which incorporate preapplied capture lines. Moreover, multimode photometer, novel test strip devices, and unique chemical analysis methods of the present invention represent a versatile, cost effective, simple, and accurate system which can quantify the amount of a chemical substance present in a sample that has not heretofore been available via prior art bioassay test strips.

According to a first aspect of the present invention, there is provided a novel magnetic chromatography method which consists of the steps of contacting activated magnetic particles suspended in a reaction mixture with a chromatographic medium (e.g., test strip or chromatographic plate), and thereafter applying a magnetic field thereto. As the activated magnetic particles flow laterally within the plane of the medium they encounter the applied magnetic field. The applied magnetic field attracts the magnetic particles forming a magnetic barrier that selectively retains magnetic particles while allowing the reaction mixture to continue to flow laterally there across. As such, there is thus eliminated the conventional capture lines formed by bound receptors that are utilized in prior art immunoassays. In this regard, a capture line is in effect assembled during the assay. Advantageously, the magnetic chromatography assay methods of the present invention allow test strips and the like to be manufactured without preapplied capture lines. However, the methods of the present invention also anticipate a magnetic chromatography test strip having both preapplied capture lines and capture lines formed during the bioassay using magnetic chromatography as may be desired for a specific application.

The novel methods of the present invention may further deploy one or more applied magnetic field source(s) applied to the chromatography test strip assembly to detect multiple spectrophotometric analysis. For example, a common bar magnet or magnetic strip can be attached to the test strip backing with adhesive at one or more locations. Alternately, the magnetic source can be external to the test strip assembly whereby the magnetic source is selectively positioned in close proximity with the test strip while magnetic particles flow laterally therewithin. In preferred embodiments of the present invention, the source of the applied magnetic field may comprise either permanent magnets or electromagnets.

The present invention further includes the use of a novel analyzer comprised of a multimode photometer which can measure front surface fluorescence, luminescence and reflectance at a single focal point on the test strips of the present invention. According to a preferred embodiment, the multimode photometer consists of a base and optical canopy which collectively define an optical tunnel into which at least one test strip may be disposed. The chamber may include a magnetic source or be designed to be placed in close proximity to a magnetic source such that the test strip having activated magnetic particles flowing laterally therewithin may be caused to become substantially bound at a specific site or sites upon the test strip. When so arranged, a light or radiation source may be focused upon the test strip disposed within the optical tunnel such that the light or radiation may be aligned with the magnetic source and the reflected or emitted light from the test strip analyzed for analyte presence. Light and radiation of differing wave lengths may be utilized to determine the presence of appropriate analytes as per conventional spectrophotometric analysis. Optical filters and photodetectors may further be deployed as may be necessary for a particular spectrophotometric applications.

It is therefore an object of the present invention to provide a novel magnetic chromatography assay and method utilizing a test strip format that has greater sensitivity and reproduceability than prior art test strip assays.

Another object of the present invention is to provide a novel magnetic chromatography assay and method that utilizes a test strip format, but dispenses with a need to form a capture line by binding receptors to a test membrane.

Another object of the present invention is to provide a novel magnetic chromatography assay and method that can be arrayed in a test strip format and utilized to provide quantitative analysis.

Another object of the present invention is to provide a novel magnetic chromatography assay and method that may be adapted to provide quantitative and qualitative analysis for multiple analytes.

Another object of the present invention is to provide a novel magnetic chromatography assay and method that is easy to use, of simple construction, and inexpensive to manufacture.

Another object of the present invention is to provide a novel magnetic chromatography assay and method that may be utilized to provide spectrophotometric analysis, including but not limited to, surface reflectance, surface fluorescence, and surface luminescence.

Another object of the present invention is to provide a novel magnetic chromatography assay and method which may be configured to perform individual sample analysis, batch sample analysis, and linear-array analysis.

Another object of the present invention is to provide a novel magnetic chromatography assay and method wherein such assay may be configured to be reusable or disposable.

Another object of the present invention is to provide a novel magnetic chromatography assay and method which will accommodate conventional reagents prepackaged in unit doses.

Another object of the present invention is to provide a novel magnetic chromatography assay and method that can be used for quantitative, semi-quantitative, and qualitative immunoassay of analytes and DNA hybridization assays.

Another object of the present invention is to provide an optical analyzer consisting of a multimode photometer for performing spectrophotometric analysis, including but not limited to, surface reflectance, surface fluorescence, and surface luminescence.

Another object of the present invention is to provide an analyzer consisting of a multimode photometer which is of simple construction, easy to utilize, and may be configured to perform individual sample analysis, batch sample analysis, and linear-array analysis.

Another object of the present invention is to provide an analyzer consisting of a multimode photometer that, when utilized in conjunction with the magnetic chromatography assays of the present invention, may be utilized to quantitate the amount of a given analyte at a fixed location on a test strip assay, irrespective of orientation of such assay and lateral flow of reaction mixture utilized therewith.

FIGURE DESCRIPTIONS

FIG. 1b is an exploded view of the components comprising the assay test strip depicted in FIG. a.

FIG. 1c is a side view of the assay depicted in FIG. 1a.

FIG. 2b is a side view of the assay test strip depicted in FIG. 2a.

DETAILED DESCRIPTION OF THE PREFERRED EMBODIMENT

The following detailed description and the accompanying drawings are provided for the purpose of describing certain presently preferred embodiments of the invention only, and are not intended to limit the scope of the claimed invention in any way. In this regard, there is disclosed herein a novel assay system and method that, unlike prior art assay systems, and in particular test strip assays, can quantitatively and qualitatively detect the presence of an analyte, control, calibrator, or combination thereof in a given fluid sample with extraordinary precision and reproduceability. Moreover, the novel assays and methods of the present invention provide all of the advantages associated with conventional test strips assays insofar as the same need not undergo remote analysis at a laboratory facility and further, do not require handling by trained professionals. There is further provided a novel analyzer, which comprises a multimode photometer, is useful in conducting spectrophotometric analysis in conjunction with the assays and methods of the present invention.

Figure 1A:
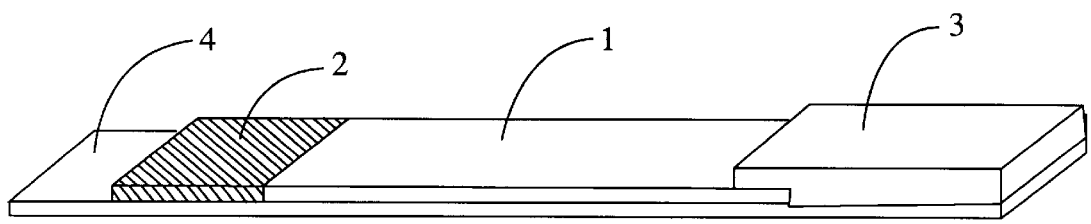
FIG. 1a is a perspective view of an assay test strip for using the practice of the methods of the present invention, said test strip being constructed in accordance to a first preferred embodiment.
Figure 1B:
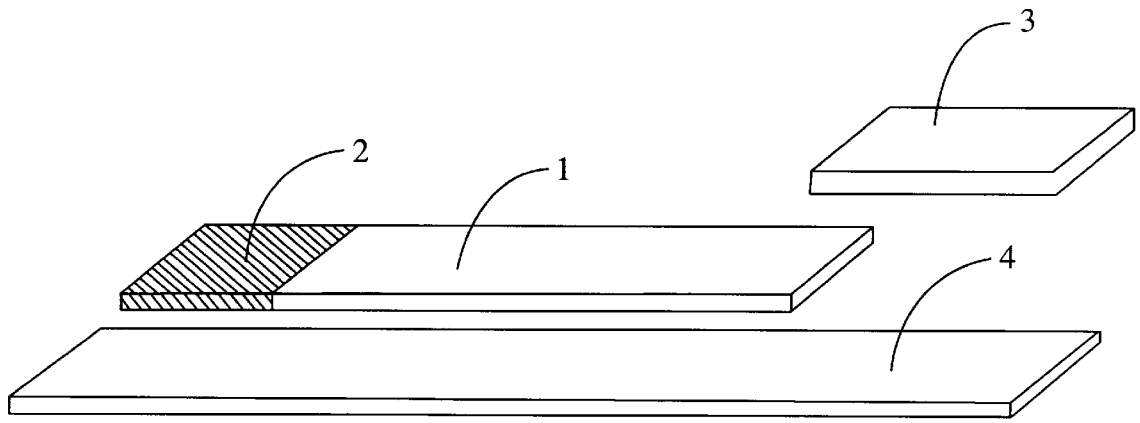
Figure 1C:
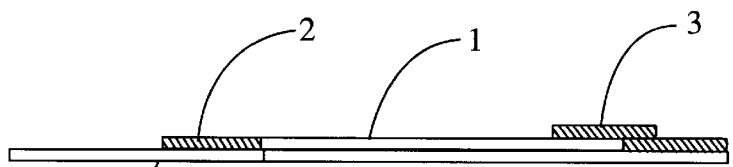

Referring now to the drawings, initially to FIGS. 1a–1c, there is shown a preferred embodiment of a test strip for use in magnetic chromatography. The test strip is comprised of a test membrane 1 having a reagent zone 2 at its one end and an absorbent pad 3 at its other end. These components are attached to a backing 4 made of plastic or other suitably rigid material. Similar to prior art test strips, the test strip is simple to manufacture by lamination.

Figure 2A:
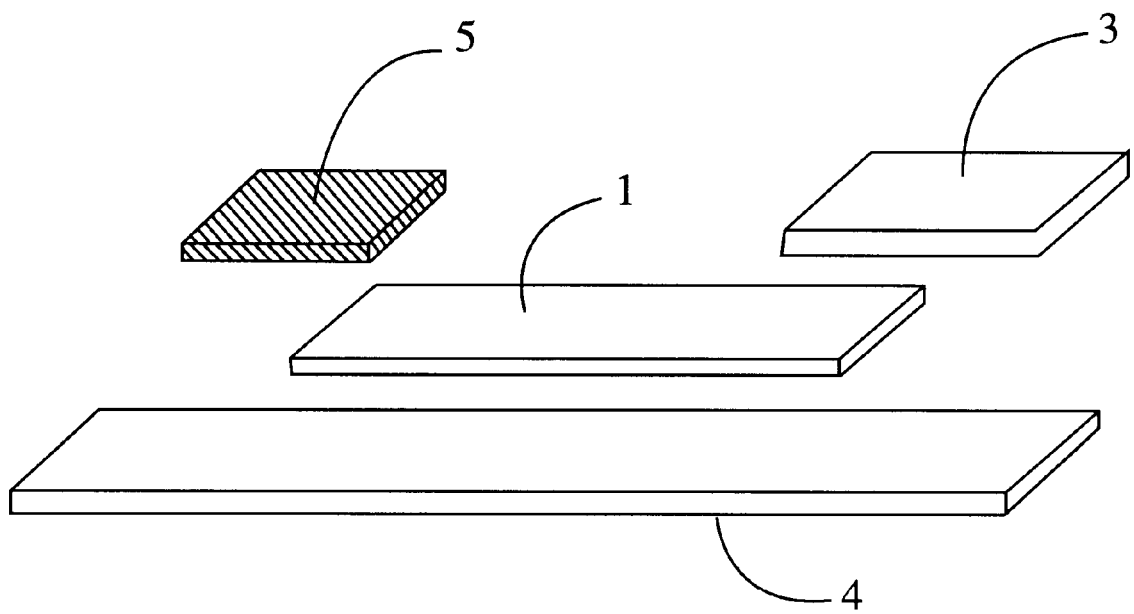
FIG. 2a is an exploded perspective view of an assay test strip constructed in accordance with a second preferred embodiment of the present invention.
Figure 2B:
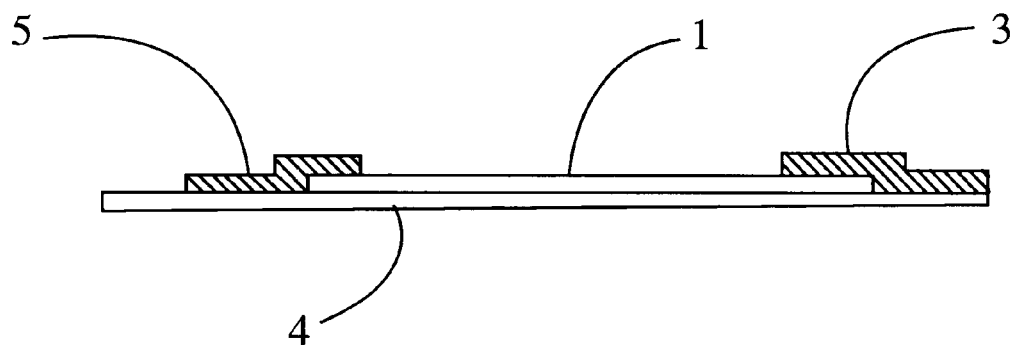

Another embodiment of the test strip for use in the practice of the present invention is shown in FIGS. 2A and 2B. In this embodiment of the invention, there is provided a reagent pad 5 at one end and absorbent pad 3 at the respective other end. In this regard, the reagent pad 5 is shown partially overlapping the test membrane 1 to thus produce a greater degree of saturation thereacross, as may be desired for a given application.

In either of the test strip embodiments depicted in FIGS. 1a–1c and FIG. 2a–2b, it will be readily understood and appreciated by those skilled in the art that the same are designed to produce a lateral flow or path of migration that extends from the reagent pad 5 to the absorbent pad 3 at the other end. As per conventional test strip assays, the lateral flow of a reaction mixture across the test membrane 1 provides a basis for conducting chemical analyses over a given surface area (i.e., the test membrane 1).

Unlike prior art test strip assays, however, the assays and methods of the present invention do not utilize a capture barrier formed by bound receptors formed along a portion of the test membrane 1, but rather utilize a novel magnetic approach to generate such capture lines. In this regard, due to the novel methods and systems by which capture lines are generated via the present invention, it will be recognized that although the test strip configurations depicted in FIGS. 1 and 2 may be readily utilized in the practice of the present invention, the only essential element thereof comprises a chromatographic medium, such as a test strip or chromatographic plate, upon which a test sample may flow laterally thereacross. Accordingly, it will be understood that a path of migration need not necessarily be formed, as per conventional test strips and the like, in order to practice the present invention.

Test Membrane

The test membrane 1 can be selected from any available material having appropriate thickness, pore size, lateral flow rate, and color. It is preferred that the test membrane be made from a material which has a low affinity for the analyte and test reagents. This is to minimize or avoid pretreatment of the test membrane to prevent nonspecific binding of analyte and/or reagent. Polyester is an example of a suitable test membrane material.

Reagent Pad

The (optional) reagent pad 5 can contain all or a portion of the reagents necessary to complete the assay. Reagents can include a capture ligand and reporter ligand which specifically bind different regions of the analyte to be detected in a given sample. The capture ligand can be covalently bound or absorbed to the surface of magnetic particles. Capture ligands can also be bound indirectly using binding partners such as anti-IgG antibody, streptavidin/biotin, and others. The reporter ligand is covalently bound to a dye, particle, radioisotope, or enzyme which produce fluorescence or luminescence. The reagent pad 5 can also contain stabilizers, buffers, surfactants and other agents which improve the performance of the assay. The reagent pad 5 receives the sample and all subsequent liquid reagents used to perform the assay.

The reagent pad 5 also can be selected from any available material having appropriate thickness, pore size, and flow rate. It is preferred that the reagent pad be made from a material which has a low affinity for the analyte and test reagents. Again, this is to minimize or avoid pretreatment of the reagent pad 5 to prevent non20 specific binding of analyte and/or reagent. Polyester and porous polyethylene are examples of suitable reagent pad 5 materials. The reagent pad 5 should be of sufficient size and void volume to accept the entire sample volume.

In some embodiments of the invention the reagent pad 5 may not be a physically separate component. Rather, instead the reagents can be stored in a reagent zone 2 formed on the test membrane 1 itself. In other embodiments of the invention, the reagent pad 5 does not contain reagents and instead is used as a liquid reagent receiving pad. As will be appreciated by those skilled in the art, by forming such reagent zones upon the test membrane as a substitute for reagent pads, the cost and complexity of manufacturing is substantially reduced insofar as the reagent pad component may be eliminated altogether. In this regard, the non-binding properties of the test membrane, coupled with the ability to form a capture line magnetically, as discussed more fully below, eliminates the need to design a test strip whereby a fluid sample must necessarily flow sequentially in one direction so that a given fluid sample with reagents thoroughly and precisely comes into contact with a conventional capture zone defined by a multiplicity of bound antibodies.

Absorbent Pad

The (optional) absorbent pad 3 should have absorbent capacity sufficient to contain all liquid volumes used during the test procedure. Cotton fiber and absorbent paper are examples of suitable absorbent pad 3 materials. As discussed above, however, the absorbent pad is optional insofar as the chromatographic medium utilized in the practice of the present invention may merely consist of a test membrane or chromatographic plate and does not necessarily require the use of an absorbent pad to produce or generate a direction of flow or path of migration for a given test sample, as is typically required in prior art assay strips.

Backing

The magnetic chromatography test strip backing 4 can be made of plastic, glass or other suitably rigid material. The backing length can exceed the length required to support the test membrane and pads, as may be desired to serve several functions. For example, such extended backing length can provide a handle or it can display information such as bar codes, fluorescent marks, and colored marks which can aid in the calibration of the individual test strip and multimode photometer, as discussed more fully below.

Figure 5A:
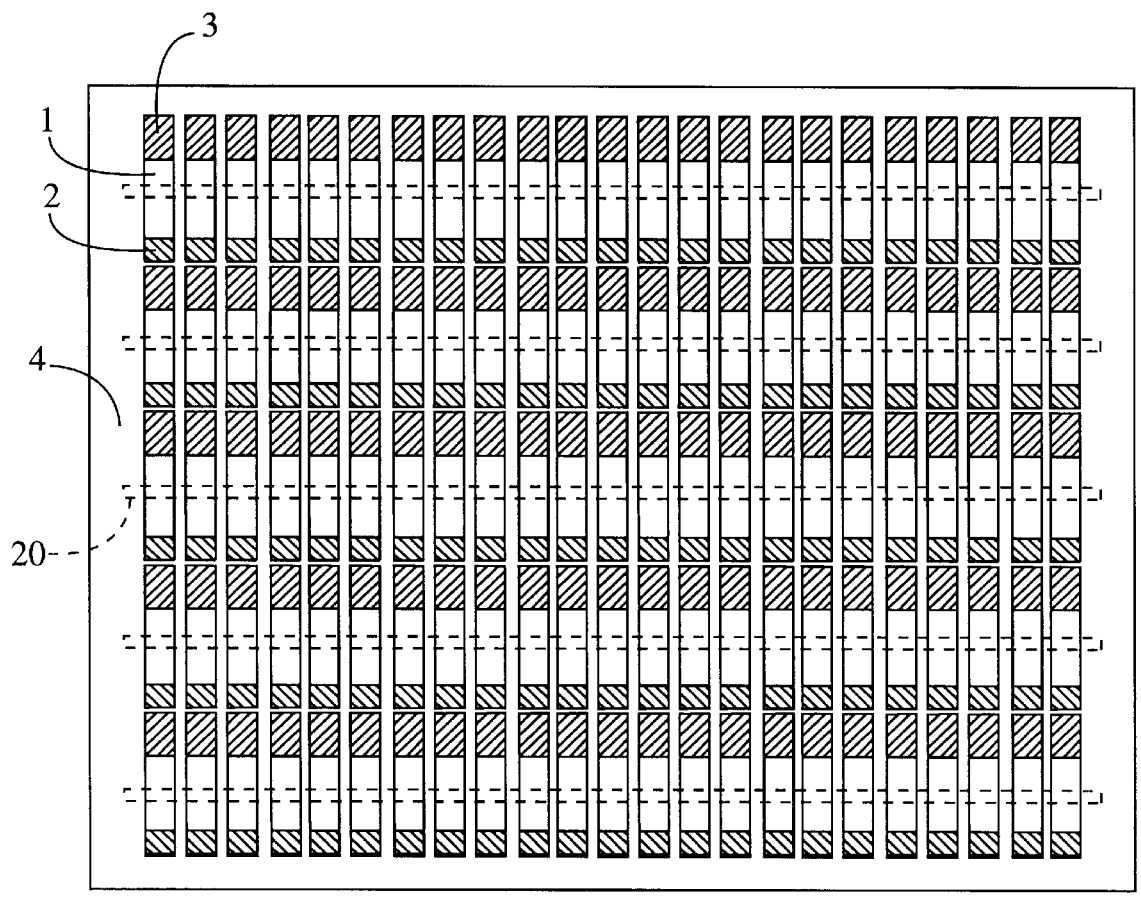
FIG. 5a is a top view of a multiplicity of test strips arrayed in parallel rows on a common backing for use in detecting the presence and quantity of one or more analytes from a plurality of samples.
Figure 5B:
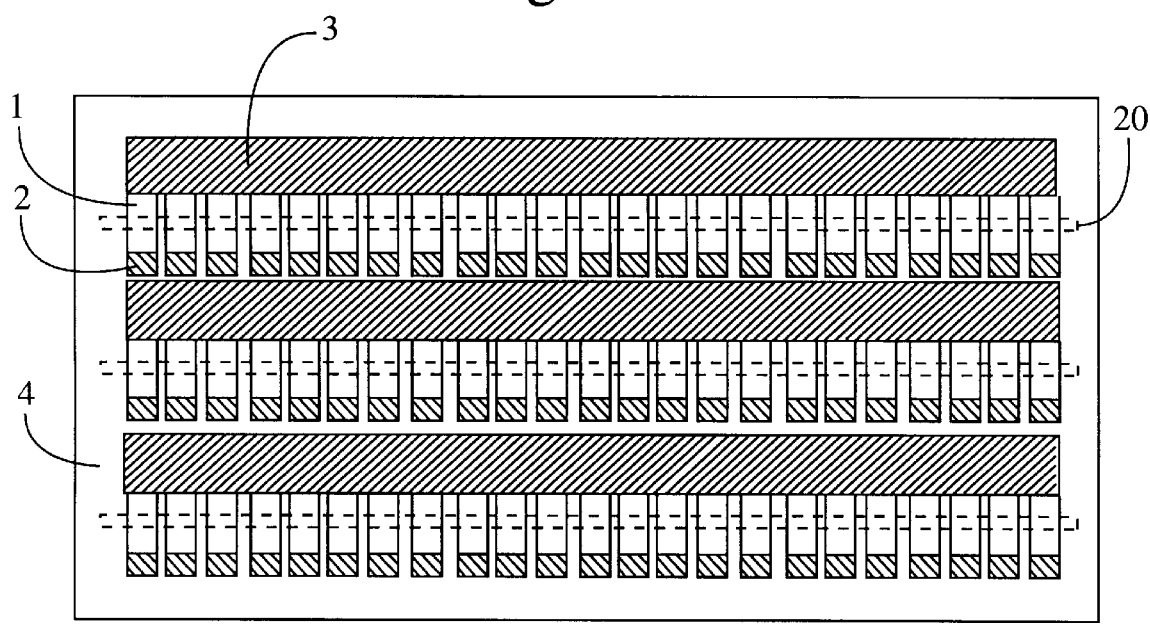
FIG. 5b is a top view of a muiplicity of test strips utilizing a single-common absorbent pad having fluid contact with a multiplicity of test membranes, the latter being arranged in a generally linear fashion.

In order to analyze a multiplicity of samples in a single analysis, there is further disclosed herein certain novel assay strips for performing such function. Referring now to FIG. 5a, there is shown a top view of a multiplicity of test strips arrayed in parallel rows on a common backing 4. The backing 4 has a top side and bottom side and can be in sheet or roll form and is preferably manufactured from an opaque plastic sheet material of appropriate color, thickness, and rigidity. Each respective test membrane 1 is sufficiently spaced to avoid fluid contact between adjoining test membranes 1. An absorbent pad 3 is preferably positioned to be in fluid contact at one end of the test membrane 1. FIG. 5b shows a top view of test strips manufactured using a single common absorbent pad 3 having fluid contact with all test membranes in a given row. Placement of test membranes 1 and absorbent pads 3 are such that multiple parallel rows of test strips are advantageously manufactured on a sheet or continuous web of backing 4. Each row of test strips is positioned with adequate spacing such that individual test strips for different rows are not in fluid contact with each other.

In order to identify the presence of a particular analyte, control, calibrator, or combination thereof, these novel methods of the present invention deploy a magnetic field at a specific site upon the test membrane portion of the test strips of the present invention. Such magnetic field, in which may be generated by any type of magnetic source, such as a permanent magnet or an electromagnet, is selectively positioned such that when applied to a portion of the test membrane, magnetic particles present within a given sample that are flowing laterally across the test membrane will become substantially bound at the specific site where the magnetic field is applied. In this regard, the applied magnetic field attracts the magnetic particles forming a magnetic barrier that selectively retains magnetic particles, with the analyte of interest having complexed thereon with appropriate labels bound thereto, while allowing the remainder of the reaction mixture to continue the flow laterally across such barrier or zone.

With respect to those strips depicted in FIG. 5a and 5b, to generate the desired capture zones of lines, a magnetic barrier is formed using a bar magnet(s) 20 laminated or placed in close proximity to the bottom side of backing 4. The bar magnet(s) or magnetized rail(s) 20 is positioned perpendicular to the test membrane(s) 1 in each row and between said test membrane(s) 1 fluid receiving and absorbent ends. A reagent zone 2 is positioned at the fluid receiving end of each test membrane.

By selectively applying the magnetic field about or upon the test strip, a capture line is magnetically assembled thereon insofar as magnetic particles are substantially immobilized by the magnetic field at a specific site of sites situated across the test membrane. The remaining reaction mixture components which are not magnetically bound thus continue to flow laterally within the test membrane, typically in a path of migration toward an absorbent pad. Advantageously, such method allows more than one analyte, control, calibrant, or combination of these to be quantitatively assayed on a single test strip. Accordingly, it is an object of this invention to provide a useful method for the performance of assays, e.g. biological assays.

While the test strips depicted in FIGS. 1a–1c and 2a–2b depict only one section of test membrane disposed between a reagent pad and an absorbent pad, it will be recognized by those skilled in the art that when more than one analyte, control, calibrator, or combination thereof are to be assayed within a test solution using a single test strip, a cascade of reagent zones or pads can be placed down stream from the first applied magnetic field. Several schematic examples of flow test strip assemblies which can be used with magnetic chromatography are given:

Single Assay reagent zone 1/test membrane//absorbent pad reagent pad 1//test membrane//absorbent pad Multiple Assay reagent zone 1/test membrane/reagent zone 2/test membrane//absorbent pad reagent pad 1//test membrane//reagent pad 2//test membrane//absorbent pad Opposing Multiple Assay reagent zone 1/test membrane//absorbent pad//test membrane/reagent zone 2 reagent pad 1//test membrane//absorbent pad//test membrane//reagent pad 2 where:
  symbol / designates a phase boundary within a single chromatographic medium; and
  symbol // designates a union of two separate mediums (chromatographic and other).

As a consequence, the multiple assay examples given causes test solution to encounter two groups of magnetic particles. The flow of test solution is unilateral moving from reagent zone or pad 1 at one end of the test strip to absorbent pad at the opposite end of the test strip. Magnetic barriers are positioned at each test membrane. The first magnetic barrier is positioned across the test membrane prior to reagent zone or pad 2 while the second magnetic barrier is positioned across the test membrane prior to the absorbent pad. Reagents from reagent zone or pad 2 can be used to analyze additional analytes in the test solution or can be used to perform calibration or quality control.

The opposing multiple assay example given will allow assay of identical analytes from separate test solutions. This is advantageous when a calibrator must be assayed simultaneously with a test sample. The flow of test solution is from each reagent pad or zone toward a single common absorbent pad. Magnetic barriers are positioned across each test membrane. It is also anticipated by the invention that magnetic chromatography can be used with other multiple assay test strip configurations including rosettes, parallel arrays, and others.

In order to manipulate the width (i.e., surface area) of the capture line formed by the application of a magnetic field to the test strip, it has been unexpectedly discovered that the width of such capture line may be selectively controlled depending upon the number of magnets and/or degree of magnetic force applied to the test membrane. In this regard, it has been discovered that by stacking multiple magnets upon one another beneath the test membrane where the captures zone is sought to be formed, the increased number of magnets applied thereto correspondingly produces an increase in the width of the capture line. As will be appreciated by those skilled in the art, by utilizing a greater degree of magnetic force, the corresponding capture line produced thereby will have a greater surface area which, as a consequence, can be utilized to determine concentration per unit area. Along these lines, it is contemplated that manipulating the magnetic field to produce a wider or narrower capture line or area may prove extremely beneficial. For example, by manipulating the width or surface area of the capture line, a means may thus be provided to facilitate the inspection of individual particles utilizing a microscope. Likewise, such selective manipulation of the capture zone may be used to isolate target cells from a population of cells, and thereafter perform microscopic inspection thereof as may be necessary for a given application.

With respect to the dimensions of such magnets that are preferably utilized in the practice of the present invention, it is currently believed that bar magnets and/or magnetized rails may be utilized whose width is between 0.003 to 3.0 inches, and whose length is between 0.010 inches to 100 inches. In this regard, it will be understood that such magnets, and in particular magnetized rails, may be sized and configured to generate any degree of magnetic field necessary to form a desired capture line and may be readily determined for a given application by one having ordinary skill in the art. The present invention further includes a novel analyzer having a multimode photometer module included therein which can measure front surface fluorescence (fluorimetry mode), luminescence (luminometry mode), and reflectance (densitometry mode) at a single focal point on a test strip. The use of multiple optical methods at a single focal point provides information regarding the quality and structure of an individual capture line as well as the amount of analyte, control, or calibrator present at the capture line. Thus an object of the invention is to minimize accuracy and precision problems associated with test strips by interrogating important test strip locations using two or more optical methods.

Figure 3B:
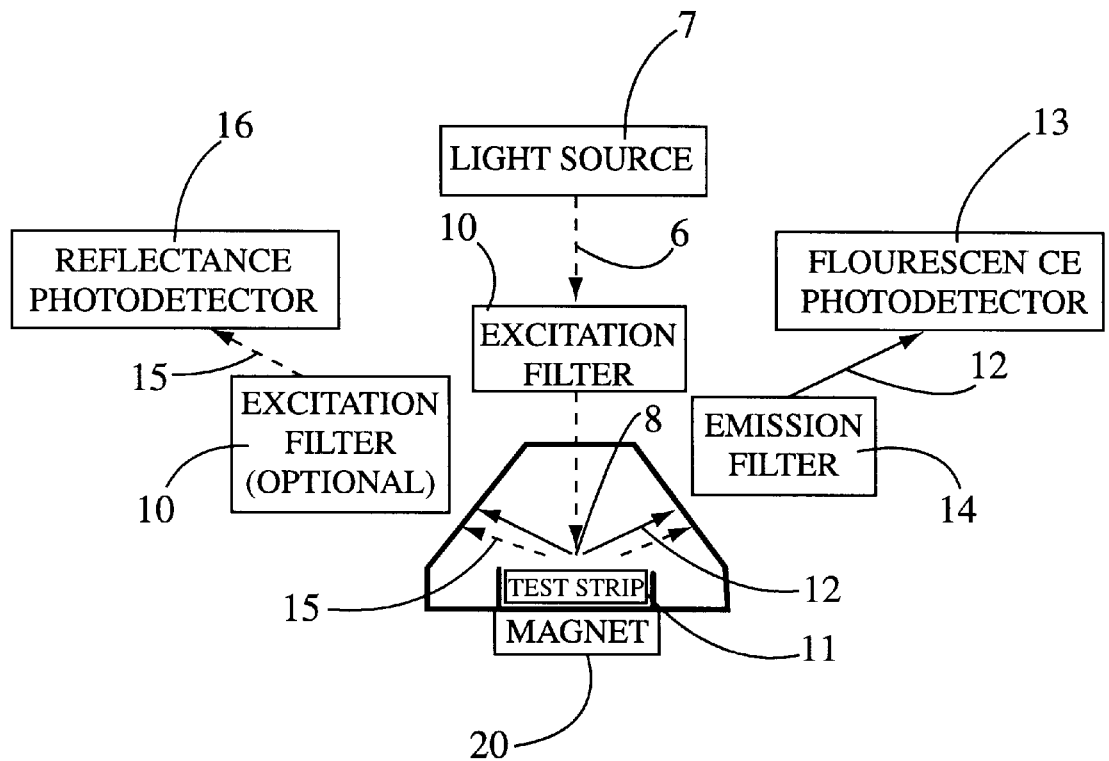
FIG. 3b is a cross-sectional view and block diagram of the multimode photometer depicted in FIG. 3.
Figure 3A:
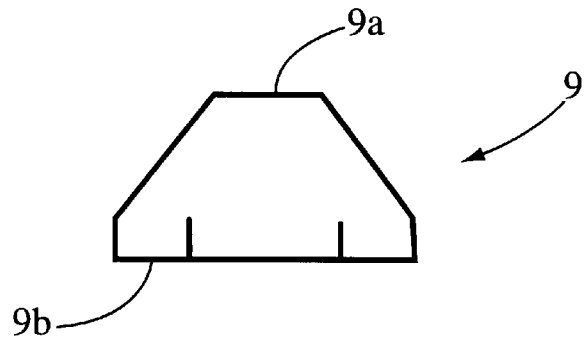
FIG. 3a is a cross-sectional view of a multimode photometer constructed in accordance with a preferred embodiment, as utilized in the practice of the methods of the present invention.

As illustrated in FIG. 3a, the multimode photometer consists of an optical canopy 9a and a base 9b which cooperate to form an optical tunnel 9. The optical tunnel 9 aligns light sources and photodetectors, with magnetic sources and test membranes, chromatographic plates, etc. to form optical paths. In this regard, base 9b includes a channel formed therein for receiving a test strip of the aforementioned variety. The base 9b further preferably includes a magnetic source fixed therein or fixed relative the channel to thus create the desired capture line at a specified location within the optical tunnel 9. For example, a magnetic source, such as a magnet, may be placed beneath the base of the optical tunnel 9b such that the test strip rests in the channel situated thereabove.

The optical canopy 9a is formed to have a ceiling through which a light source may be transmitted, and angled sidewalls through which the resultant reflected light may be emitted. As will be recognized by those skilled in the art, the multimode photometer, and more particularly the optical tunnel defined thereby, may be extruded, machined, or molded from any of a variety of suitable opaque materials, including but not limited to PVC, ABS, or anodized aluminum. As such, the optical tunnel 9 of the present invention may be fabricated inexpensively from inexpensive materials.

Referring now to FIG. 3b, there is schematically illustrated the components utilized for analyzing a test strip with the multimode photometer of the present invention. Initially, an excitation path 6 is formed from the light source 7 to a focal point 8 at the base 9b of the optical tunnel 9. As will be readily appreciated, the magnetic source incorporated into the base 9b for forming the capture line on a given test membrane or chromatographic plate will be precisely aligned with the excitation path 6 such that the path 6 is directly aimed at the capture line produced by such magnetic source. As will be appreciated, light emitting diodes (LEDs), laser diodes, mercury vapor lamps, and xenon lamps are among many suitable light sources which can be used. If necessary, an optical filter 10 can be used to select an excitation wavelength 6. This excitation filter 10 can be placed on either side of the canopy wall 9a provided, however, the same is in the excitation path 6 between the light source and test strip 11. When a test strip 11 is inserted into the optical tunnel 9, such strip is held in position at the base and intersects the excitation path 6 at the focal point 8.

Emission paths 12 are formed from the focal point to one or more photodetectors 13. Apertures are positioned using a radial geometry in the canopy wall 9a at angles which optically align each photodetector 13 with the focal point 8. Light pipes, optical fibers, and other wave guides can be used to transmit emission light to the photodetectors 13. Excitation light 6 excites fluorophores present on the test strip 11 at the focal point 8, which then emit light 12 of a longer wavelength. If luminescence is used excitation light 6 is not required and can be omitted during luminescence measurement. Emission filters 14 are used to specifically select the emission wavelength 12 of the light emitted from the fluorescer or luminescer and to remove traces of excitation light 6. As will be appreciated by those skilled in the art, such emission filter 14 can be placed on either side of the canopy wall 9a providing it is in the emission path 12 between the photodetector 13 and test strip 11.

Reflectance paths 15 are also formed from the focal point 8 to one or more photodetectors 16. Such reflectance path 15 carries both excitation 6 and emission light 12. If necessary, excitation filters 10 can be used to specifically select the excitation wavelength 6 of the light reflected from the test strip and to revoke traces of emission light 12. This excitation filter 10 can be placed on either side of the canopy wall 9a providing it is in the reflectance path 15 between the photodetector 16 and test strip 11.

The filters 10 and 14 can be of the type known in the art as interference filters, due to the way in which the same block out-of-band transmissions. In this respect, interference filters exhibit an extremely low transmission outside of their characteristic bandpass and, as such, are very efficient in selecting the desired excitation and emission wavelengths.

As will further be appreciated by those skilled in the art, an optical tunnel can have multiple focal points at which photometric measurements can be made simultaneously, which advantageously allows multiple points on a test strip to be used for sample analysis and/or calibration. In such applications, optical components, such as LEDs, photodiodes, and interference filters, may be clustered at each focal point along the optical tunnel.

Figure 4A:
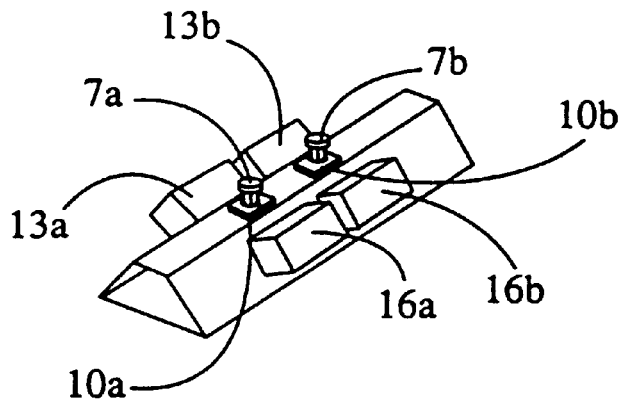
FIG. 4a is perspective view of the multimode photometer depicted in FIG. 3.
Figure 4B:
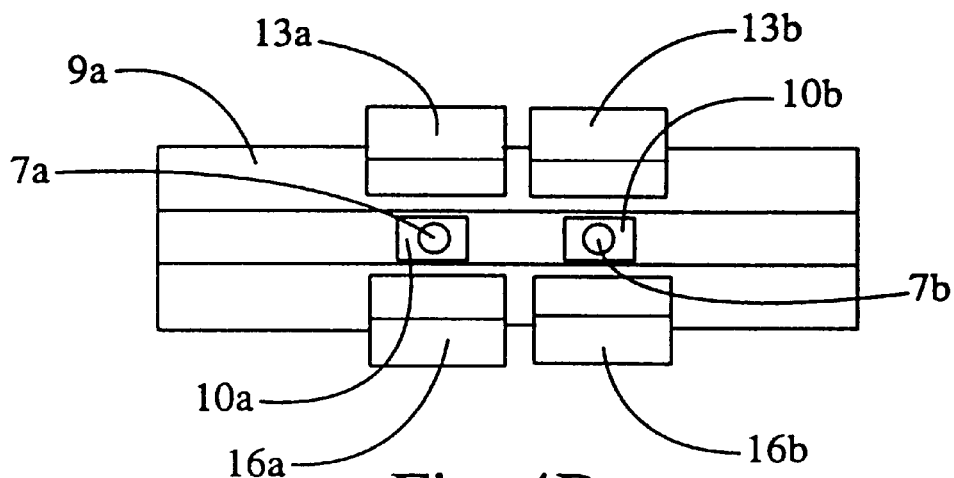
FIG. 4b is a top view of the multimode photometer depicted in FIG. 3.
Figure 4C:
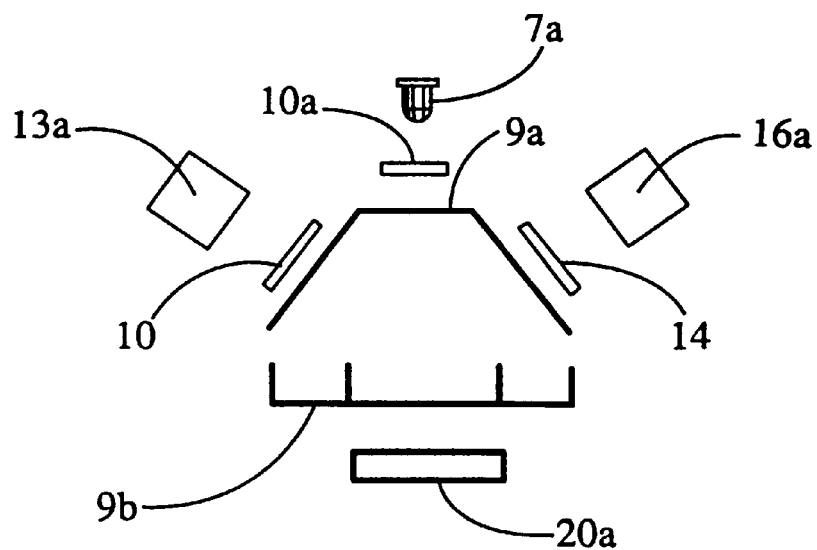
FIG. 4c is an exploded cross-sectional view of the components comprising the multimode photometer depicted in FIG. 3.

As perspectively illustrated in FIGS. 4a and 4b, there is shown different views of an optical tunnel equipped with two optical clusters as may be utilized for multispectral analysis. A light source 7 (LEDs 7a and 7b are shown) is positioned above an excitation filter 10 (filters 10a and 10b are shown) which in turn covers each excitation aperture (not shown). Two of four photodiodes 13a, 16a with filters 10,14, as shown in the cross-sectional view of FIG. 4C, are mounted on the canopy 9a. A bar magnet 20a, as shown in FIG. 4C, is positioned at the base of the optical tunnel beneath each focal point 8 such that appropriate spectrophotometric analysis may be made at each location.

Although believed to be apparent from the foregoing discussion, there is provided herebelow a variety of examples by which the novel magnetic assays and methods of the present invention may be utilized in a variety of applications. As will be appreciated by those skilled in the art, for the purpose of discussion in the following examples the term "test solution" can mean test sample, test calibrator, or test control material.

EXAMPLE 1

A test strip is manufactured according to the description given in FIG. 1. The backing 4 is extended in length beyond the absorbent pad 3 end to allow application of bar codes, fluorescent markings, and other indicators to the backing 4. Reagent zone 2 contains streptavidin conjugated magnetic particles, buffers, stabilizers, surfactants, and other reagents in dry form.

The test strip 11 is inserted absorbent pad 3 end first into the optical tunnel 9. Indicators on the test strip are interpreted as calibration information by the analyzer. For example, the analyzer verifies that the same bar code was read at both focal points 8a and 8b and stores reflectance and fluorescence values for photodetectors 13 and 16. The calibration information and measured values are used by the analyzer to verify the quality and structure of an individual capture line as well as the amount of analyte, control, or calibrator present at the capture line, and to verify the performance of each optical module.

In a separate container the operator adds a measured volume of sample to a measured volume of test reagents and mixes them to form a reaction mixture. The test reagents include biotin conjugated anti-beta HCG, and fluorescent microsphere conjugated anti-alpha HCG which cooperatively bind HCG molecules present in the sample.

A measured volume of this reaction mixture is applied to the test strip reagent zone 2 it forms a new reaction mixture which contains magnetic particles in suspension as buffers, stabilizers, surfactants, and other reagents previously dried on the reagent zone 2. The magnetic particles bind the biotin conjugate in all of its complexed forms including those which have formed a cooperative complex (sandwich assay) with HCG and the anti-alpha HCG conjugate. Thus, fluorescent microspheres are indirectly bound to magnetic particles in proportion to the amount of analyte present in the reaction mixture.

As the magnetic particles suspended in the reaction mixture flow laterally within the plane of the test strip 11 they encounter a magnetic field applied using a bar magnet 20 attached to the base 9b of the optical tunnel 9. The applied magnetic field attracts the magnetic particles forming a magnetic barrier that selectively retains the magnetic particles at the focal point 8 while allowing reaction mixture to continue to flow laterally across this barrier toward the absorbent pad 3.

A measured volume of wash solution can also be added subsequent to the addition of reaction mixture. This will reduce the amount of fluorescent microspheres retained by the test membrane 1 and magnetic particles due to nonspecific binding.

The analyzer monitors and compares photodetectors 16a and 16b measuring reflectance at the focal point 8a and 8b. The reflected light intensity at the focal point 8a decreases as the magnetic particles are retained by the magnet 20. The reflected light intensity at focal point 8b is a background (blank) measurement used to correct for differences between individual test strips and sample matrix effects. This allows the analyzer to determine whether the magnetic particles have been properly captured at focal point 8a, and to reject samples which are hemolyzed or contain elevated amounts of chromophores such as bilirubin. If the reflected light intensity is not within specification at focal points 8a and 8b during a predefined elapsed time the test is determined invalid and no result is reported.

Alternating with photodetectors 16a and 16b, the analyzer also monitors and compares photodetectors 13a and 13b measuring fluorescence. The emitted light intensity at focal point 8b is a background (blank) measurement used to correct for non-specific binding, differences between individual test strips, and sample matrix effects. The analyzer compares the blank emission measurement at 8b and test emission measurement at 8a and calculates HCG concentration.

EXAMPLE 2

Example 2 mirrors Example 1 but for the following differences:

Reagent zone 2 contains all test reagents prepackaged in unit dose dried form including: streptavidin conjugated magnetic particles, biotin conjugated anti-beta HCG, and fluorescent microsphere conjugated anti-alpha HCG which cooperatively bind HCG molecules present in the sample. Reagent zone 2 also contains buffers, stabilizers, sufactants, and other reagents in dry form.

The operator adds a measured volume of test solution directly to reagent zone 2.

EXAMPLE 3

Example 3 mirrors Example 2 but for the following differences:

Anti-alpha HCG is conjugated using alkaline phosphatase, instead of fluorescent microspheres.

A measured volume of fluorescent substrate is added to the reagent zone 2 subsequent to the addition of a measured volume of wash solution.

EXAMPLE 4

Example 4 mirrors all of the above examples but for the following differences:

Example 4 substitutes a reagent pad 5 for reagent zone 2 in each of the preceding examples.

EXAMPLE 5

A test strip is manufactured according to the prescription given in FIG. 1. The backing 4 is extended in length beyond the absorbent pad 3 end to allow application of bar codes, fluorescent markings, and other indicators to the backing 4. Reagent zone 2 contains streptavidin conjugated magnetic particles, buffers, stabilizers, surfactants, and other reagents in dry form.

In a separate container, the operator adds a measured volume of test solution (containing cells, cell lysate, total RNA) to a measured volume of test reagents and mixes them to form a reaction mixture. The test reagents include biotinylated oligo (dT) probe and a 5' fluorescent dye labeled DNA hybridization probe specific for chlamydia.

A measured volume of this reaction mixture is applied to the test strip reagent zone 2. As the reaction mixture comes in contact with the reagent zone 2 it forms a new reaction mixture which contains magnetic particles in suspension as well as buffers, stabilizers, surfactants, and other reagents previously dried in the reagent zone 2. the biotinylated oligo (dT) probe hybridizes specifically to the 3' poly(A) region of all mRNA present in the test solution. Consequentially, all mRNA is bound to the magnetic particles via a biotin/streptavidin bond. Labeled hybridization probe, in contrast, binds only target mRNA. The magnetic particles bind the biotinylated oligo (dT) probe in all of its complexed forms including those which have formed a cooperative complex (hybrid) with chlamydia mRNA and the fluorescent dye labeled DNA hybridization probe specific for chlamydia. Thus, fluorescent dye is indirectly bound to magnetic particles in proportion to the amount of chlamydia mRNA present in the reaction mixture.

As the magnetic particles suspended in the reaction mixture flow laterally within the plane of the test strip 11 they encounter a magnetic field applied using a bar magnet 20 attached to the base 9b of the optical tunnel 9. The applied magnetic field attracts the magnetic particles forming a magnetic barrier that selectively retains the magnetic particles at the focal point 8 while allowing reaction mixture to continue to flow laterally across this barrier toward the absorbent pad 3.

A measured volume of wash solution can also be added subsequent to the addition of reaction mixture. This will reduce the amount of labeled DNA probe retained by the test membrane 1 and magnetic particles due to non-specific binding.

The analyzer monitors and compares photodetectors 16a and 16b measuring reflectance at the focal point 8a and 8b. The reflected light intensity at the focal point 8a decreases as the magnetic particles are retained by the magnet 20. The reflected light intensity at focal point 8b is a background (blank) measurement used to correct for differences between individual test strips and sample matrix effects. This allows the analyzer to determine whether the magnetic particles have been properly captured at focal point 8a, and to reject samples which are hemolyzed or contain elevated amounts of chromophores such as bilirubin. If the reflected light intensity is not within specification at focal points 8a and 8b during a predefined elapsed time the test is determined invalid and no result is reported. Alternating with photodetectors 16a and 16b, the analyzer also monitors and compares photodetectors 13a and 13b measuring fluorescence. The emitted light intensity at focal point 8b is a background (blank) measurement used to correct for non-specific binding, differences between individual test strips, and sample matrix effects. The analyzer compares the blank emission measurement at 8b and test emission measurement at 8a and calculates chlamydia concentration or determines simply if chlamydia is present in the test solution.

EXAMPLE 6

Other detection methods can be used with magnetic chromatography. In this example, x-ray film is used to detect the presence of target DNA in a population of transfected cells. PCR amplification of cDNA present in each test solution is accomplished using P32 labeled nucleotides. Amplified DNA is hybridized using 5' biotin DNA hybridization probe forming a reaction mixture which is applied to the test strip reagent zone 2 containing streptavidin conjugated magnetic particles.

Utilizing a test strip of the variety depicted in FIG. 5b, a wash solution is applied to reagent zone 2 subsequent to application of the reaction mixture.

A sheet of x-ray film is placed on top of said test strip array and exposed for a suitable length of time.

A visible band is seen on the developed x-ray film whose position corresponds with a sample which has tested positive for the target DNA.

EXAMPLE 7

Example 7 mirrors Example 6 but for the following differences:

Said PCR amplification is accomplished using 5' fluorescent dye labeled primer.

Said test strip array is positioned within a fluorescent scanner.

Said fluorescent scanner detects a fluorescent band whose position corresponds with a sample testing positive for the target DNA.

EXAMPLE 8

Example 8 mirrors Example 1 but for the following differences:

Said backing 4 is a microscope slide.

Said magnet 20 is positioned above said test membrane 1, so that magnet 20 is not in contact with test membrane A fluorescent microscope is used to count individual fluorescent microspheres bound to magnetic particles.

EXAMPLE 9

A test strip is manufactured according to the description given in FIG. 1. The backing 4 is extended in length beyond the absorbent pad 3 end to allow application of bar codes, fluorescent markings, and other indicators to the backing 4. Reagent zone 2 contains streptavidin conjugated 0.86 micron magnetic particles, anti-mouse IgG conjugated 150 nm magnetic particles, buffers, stabilizers, sufactants, and other reagents in dry form.

The test strip 11 is inserted absorbent pad 3 end first into the optical tunnel 9. Indicators on the test strip are interpreted as calibration information by the analyzer. For example, the analyzer verifies that the same bar code was read at both focal points 8a and 8b and stores reflectance and fluorescence values for photodetectors 13 and 16. The calibration information and measured values are used by the analyzer to verify the quality and structure of an individual capture line as well as the amount of analyte, control, or calibrator present at the capture line, and to verify the performance of each optical module.

In a separate container the operator adds a measured volume of sample to a measured volume of test reagents and mixes them to form a reaction mixture. The test reagents include biotin conjugated goat anti-beta FSH, and fluorescent microsphere conjugated goat anti-alpha FSH which cooperatively bind follicle stimulating hormone (FSH) molecules present in the sample. The test reagents also include mouse anti-beta LH, and fluorescent microsphere conjugated goat anti-alpha LH which cooperatively bind FSH molecules present in the sample.

A measured volume of this reaction mixture is applied to the test strip reagent zone 2. As the reaction mixture comes in contact with the reagent zone 2 it forms a new reaction mixture which contains 0.86 micron and 150 nm magnetic particles in suspension as well as buffers, stabilizers, surfactants, and other reagents previously dried on the reagent zone 2. The 0.86 micron magnetic particles bind the biotin conjugate in all of its complexed forms including those which have formed a cooperative complex (sandwich assay) with FSH and the anti-alpha FSH conjugate. Thus fluorescent microspheres are indirectly bound to magnetic particles in proportion to the amount of analyte present in the reaction mixture. The 150 nm magnetic particles bind the mouse anti-beta LH conjugate in all of its complexed forms including those which have formed a cooperative complex (sandwich assay) with LH and the goat anti-alpha LH conjugate. Thus, fluorescent microspheres are indirectly bound to magnetic particles in proportion to the amount of analyte present in the reaction mixture.

As the magnetic particles suspended in the reaction mixture flow laterally within the plane of the test strip 11 they encounter a first magnetic field applied using a bar magnet 20a attached to the base 9b of the optical tunnel 9. The applied magnetic field is of sufficient strength that it provides a magnetic barrier that selectively retains the 0.86 micron magnetic particles at the focal point 8a while allowing reaction mixture including 150 nm magnetic particles in suspension to continue to flow lateral across this barrier toward the absorbent pad 3.

As the 150 nm magnetic particles suspended in the reaction mixture flow laterally within the plane of the test strip 11 they encounter a second magnetic field applied using a second bar magnet 20b (not shown) attached to the base 9b of the optical tunnel 9. The second applied magnetic field is significantly stronger than said first applied magnetic field. This second applied magnetic field provides a magnetic barrier that selectively retains the 150 nm magnetic particles at the focal point 8b while allowing reaction mixture to continue to flow laterally across this second magnetic barrier toward the absorbent pad 3.

A measured volume of wash solution can also be added subsequent to the addition of reaction mixture. This will reduce the amount of fluorescent microspheres retained by the test membrane 1 and magnetic particles due to nonspecific binding.

The analyzer monitors and compares photodetectors 16a and 16b measuring reflectance at the focal point 8a and 8b.

The reflected light intensity at the focal point 8a decreases as the magnetic particles are retained by the first magnet 20a and second magnet (not shown). The reflected light intensity at focal points 8a and 8b are measurements used to determine whether the magnetic particles have been properly captured at focal points 8a and 8b. If the reflected light intensity is not within specification at focal point 8a and 8b during a predefined elapsed time the test is determined invalid and no result is reported.

Alternating with photodetectors 16a and 16b, the analyzer also monitors and compares photodetectors 13a and 13b measuring fluorescence. The emitted light intensity at focal points 8a and 8b are used to calculate FSH and LH concentrations respectively. The analyzer compares these emitted light intensities with those of test solutions containing known concentrations of FSH and LH, based upon such parameters, and calculates FSH and LH concentrations.

It is to be further understood that various additions, deletions, modifications and alterations may be made to the above-described embodiments without departing from the intended spirit and scope of the present invention. In this regard, it should expressly be recognized that in addition to the magnetically-generated capture lines formed herein, additional capture lines may be formed as per conventional test strip assays which incorporate the use of bound receptors formed upon a test membrane. Accordingly, it is intended that all such additions, deletions, modifications and alterations be included within the scope of the following claims.

What is claimed is:

1. A magnetic chromatography method for performing a bioassay comprising the steps:
    a) providing a chromatographic medium;
    b) providing a magnetic field;
    c) providing a reaction mixture suspected of, containing an analyte, a reporter ligand that binds to said analyte, and a quantity of magnetic particles with capture ligands for binding said analyte immobilized thereon suspended therein;
    d) contacting said chromatographic medium with said reaction mixture such that said reaction mixture flows laterally across said chromatographic medium;
    e) applying said magnetic field at a site upon said chromatographic medium, said magnetic field being so applied such that a majority of said magnetic particles suspended within said reaction mixture is caused to become captured upon said medium at said site where said magnetic field is applied; and
    f) analyzing said majority of magnetic particle captured upon said chromatographic medium.

2. The magnetic chromatography method of claim 1 wherein in step b), said magnetic field is generated by a magnet.

3. The magnetic chromatography method of claim 2 wherein in step b), said magnetic field is provided by a magnetic rail having a width between 0.003 inches and 3.0 inches, and having a length between 0.010 inches and 100 inches.

4. The magnetic chromatography method of claim 1 wherein in step b), said magnetic field is generated by an electromagnet.

5. The magnetic chromatography method of claim 1 wherein in step e), said magnetic field is applied by positioning a magnet in close proximity said chromatographic medium.

6. The magnetic chromatography method of claim 1 wherein in step c), said magnetic particles having an analyte, receptor, and label complexed therewith.

7. The magnetic chromatography method of claim 5 wherein said label comprises a detectable chemical moiety selected from the group consisting of radioactive, fluorescent, enzymatic, and dye moieties.

8. The magnetic chromatography method of claim 1 wherein in step b), said magnetic field is provided by at least two (2) magnets.

9. The magnetic chromatography method of claim 1 wherein in step c), said magnetic particles have a diameter ranging between 1 nm to 10 microns.

10. The magnetic chromatography method of claim 1 wherein in step a), said chromatographic medium comprises a test membrane.

11. The magnetic chromatography method of claim 1 wherein in step a), said chromatographic medium comprises a chromatographic plate.

12. The magnetic chromatography method of claim 1 wherein in step a), said chromatographic medium comprises a test, strip, said test strip comprising a backing having a liquid receiving end, test membrane and liquid absorbent end formed thereon in a sequential fashion, said test membrane being dispose intermediate to said liquid receiving end and said liquid absorbent end such that said liquid receiving end, test membrane and liquid absorbent end cooperates to define a lateral directions of flow.

13. The magnetic chromatography method of claim 1 wherein in step (c), said capture ligand is covalently bound to said magnetic particles.

14. The magnetic chromatography method of claim 1 wherein in step (c), said capture ligand is absorbed to the surface of said magnetic particles.

15. The magnetic chromatography method of claim 1 wherein step (c), said analyte is present in the sample and said analyte is selected from the group consisting of a control analyte and a calibrator analyte.

16. A magnetic chromatography method for sequentially performing a multiplicity of bioassays comprising the steps:
    a) provide a multiplicity of chromatographic mediums;
    b) providing a magnetic field;
    c) providing at least one reaction mixture suspected of containing at least one analyte at least one reporter ligand that binds to said at least one analyte and a quantity of magnetic particles with capture ligands for binding to at least one of said analytes immobilized thereon suspended therein;

d) contacting said multiplicity of chromatographic mediums with said at least one reaction mixture such that said at least one reaction mixture flows laterally across each respective one of said mediums;

e) applying said magnetic field at dedicated sites upon respective ones of said multiplicity of chromatographic mediums, said magnetic field being so applied such that a majority of said magnetic particles suspended within said at least one reaction mixture is caused to become captured upon a respective one of said multiplicity of chromatographic mediums at said sites where said magnetic field is applied;

f) analyzing said majority of magnetic particles captured upon said chromatographic mediums.

17. The magnetic chromatography method of claim 16 wherein in step a), said chromatographic medium is selected from the group consisting of test membranes and chromatographic plates.

18. The magnetic chromatography method of claim 16 wherein in step b), said magnetic field is generated by a magnetic rail.

19. The magnetic chromatography method of claim 18 wherein in step b), said magnetic rail is situated in close proximity to dedicated sites upon respective ones of said multiplicity of chromatographic mediums.

* * * * *